United States Patent [19]

Debras et al.

[11] Patent Number: 5,171,331
[45] Date of Patent: Dec. 15, 1992

[54] PROCESS FOR PRODUCING GASOLINE

[75] Inventors: Guy L. G. Debras, Belgrade; Raymond M. Cahen, Bruxelles; Georges E. M. J. De Clippeleir, Sint-Pieters-Leeuw, all of Belgium

[73] Assignee: Fina Research, S.A., Feluy, Belgium

[21] Appl. No.: 583,578

[22] Filed: Sep. 17, 1990

Related U.S. Application Data

[63] Continuation-in-part of Ser. No. 8,870, Jan. 29, 1987, abandoned.

[30] Foreign Application Priority Data

Jan. 29, 1986 [LU] Luxembourg ............................ 86280

[51] Int. Cl.$^5$ ................................................. C10L 1/18
[52] U.S. Cl. .................................... 44/449; 568/697
[58] Field of Search ........................... 568/697; 44/449

[56] References Cited

U.S. PATENT DOCUMENTS 4,377,393 3/1983 Schleppinghoff ...................... 44/449
4,417,088 11/1983 Miller .................................. 585/533

Primary Examiner—Ellen McAvoy
Attorney, Agent, or Firm—William D. Jackson; John K. Abokhair; M. Norwood Cheairs

[57] ABSTRACT

A process for production of gasoline comprising oligomerizing a $C_2$–$C_6$ olefin containing feedstock over an intermediate pore size siliceous crystalline molecular sieve catalyst. The catalyst may take the form of silicalite, halogen stabilized silicalite, or a zeolite. Water may be supplied to the oligomerization reaction. The product from the oligomerization reaction is then subjected to an etherification reaction in the presence of methanol over an acid cation exchange catalyst to provide a gasoline product of enhanced octane number.

35 Claims, 1 Drawing Sheet

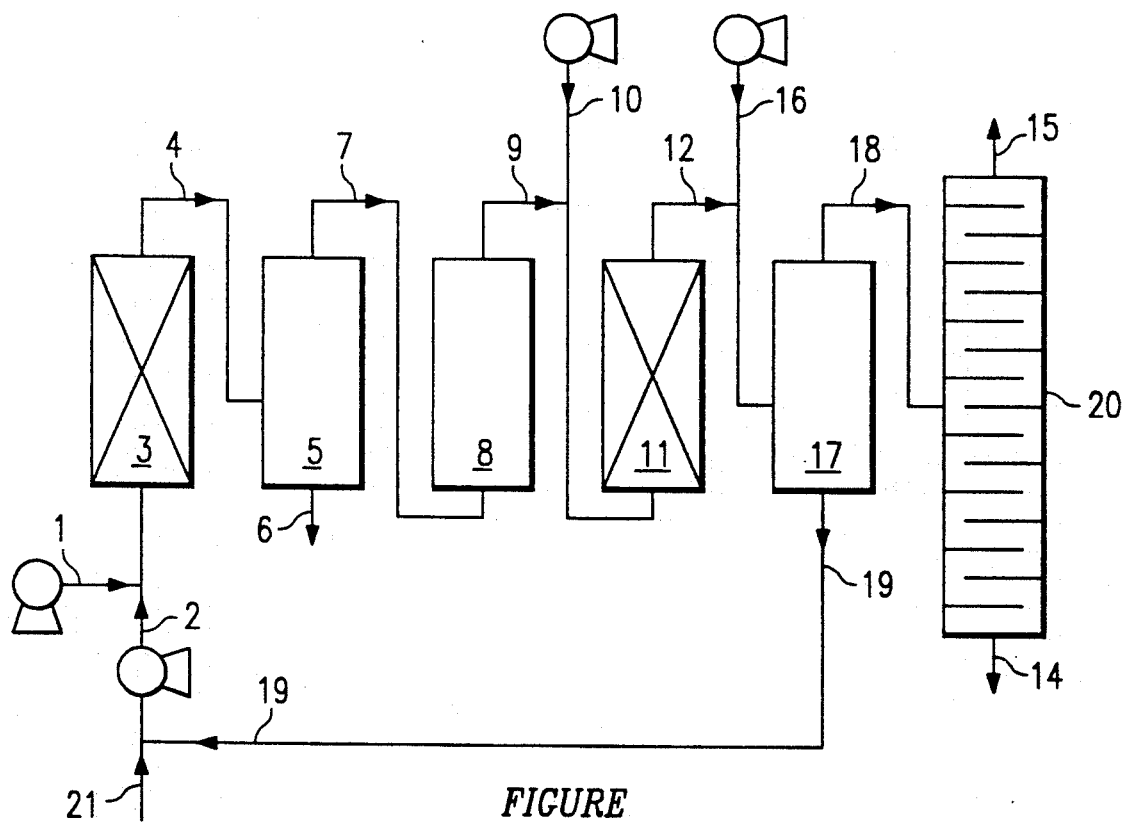
*FIGURE*

PROCESS FOR PRODUCING GASOLINE

This application is a continuation-in-part of U.S. patent application Ser. No. 008,870, filed Jan. 29, 1987, now abandoned.

The present invention relates to a process for the production of gasoline having an improved octane number.

The use of lead-free gasoline or gasoline having a reduced lead content is increasingly mandated. Accordingly, procedures for improving the octane number of gasoline, which do not require lead additives are becoming increasingly important.

Gasoline range materials are conventionally prepared by standard oligomerization of olefinic hydrocarbons in the presence of phosphoric acid-containing catalysts. These materials essentially consist of dimers. They are upgraded by the addition of lead-free gasoline anti-knock additives, among which methyl tert-butyl ether (MTBE) is most often used. Other additives, such as tert-amyl methyl ether (TAME), and other types of additives, such as alcohols, have also been proposed.

Methyl tert-butyl ether and other branched-chain aliphatic esters useful as octane enhancing blending agents may be produced by processes known by those skilled in the art. U.S. Pat. No. 4,503,263 to Olah discloses the production of methyl tert-butyl ether by the reaction of methyl alcohol and isobutylene over perfluorinated alkanesulfonic acid catalysts. U.S. Pat. No. 4,503,274 to Al-Muddarris discloses a process for producing methyl tert-butyl ether wherein n-butane is isomerized followed by dehydrogenation to produce isobutane/isobutene mixture which is reaction under etherification conditions with methanol derived from synthetic gas. U.S. Pat. No. 4,502,265 to Schleppinghoff et al. discloses a process for the production of methyl tert-butyl ether in which a $C_4$ fraction containing a mixture of iso- and normal-butanes and butenes is supplied through sequential etherification reactors, each of which contain a suitable acid cation exchange catalyst. The output from the reactor train is supplied to a distillation column for recovery of the ether product.

More recently, gasoline products have been prepared by oligomerization processes which involve the conversion of normally gaseous olefins (either alone or in admixture with paraffins) into an olefinic gasoline blending stock by passage over various catalysts of the intermediate pore size siliceous crystalline molecular sieve type.

Such intermediate pore size molecular sieves are disclosed in U.S. Pat. No. 4,417,088 to Miller. By "intermediate pore size siliceous crystalline molecular sieve" as used in Miller, is meant two classes of silica containing crystalline materials. The first class includes materials which, in addition to silica, contain significant amounts of alumina. These crystalline materials are usually called "zeolites", i.e., crystalline aluminosilicates. As disclosed in Miller, such ZSM zeolites include ZSM-5, ZSM-11, ZSM-12, ZSM-21, ZSM-23, ZSM-35 and ZSM-38. The second class of materials are essentially alumina-free silicates and include crystalline silica polymorphs - specifically silicalite.

One advantage of such oligomerization processes lies in the higher liquid hourly space velocities (LHSV), typically 30–40, which may be used. This is in contrast to the oligomerization processes carried out over phosphoric acid containing catalysts which typically only allow LHSV values of 1–4. Another advantage is that the siliceous crystalline molecular sieves can be regenerated, whereas phosphoric acid-containing catalysts cannot be reused.

Many oligomerization processes have been disclosed in which olefin oligomerization is carried out over aluminosilicate zeolites. For example, U.S. Pat. No. 3,960,978 to Givens discloses oligomerization of $C_2$–$C_5$ olefins, either alone or in admixture with $C_1$–$C_5$ paraffins, over ZSM-5 type zeolites such as ZSM-5 and ZSM-11 with a controlled alpha value and reduced aromatization activity. The product is an olefinic gasoline pending fraction having no more than 20% aromatics. U.S. Pat. No. 4,021,502 to Plank discloses the conversion of similar olefin or olefin-paraffin feedstocks over crystalline aluminosilicates identified specifically as ZSM-4, ZSM-12, ZSM-18, chabazite or zeolite beta.

U.S. Pat. No. 4,150,062 to Garwood discloses the conversion of a $C_2$–$C_4$ olefin feedstock to produce gasoline components in which water is co-fed in an amount of about 0.5–15 moles of water/mole of olefin feedstock. Olefin conversion in the presence of water co-feed was about 95% after 16 days, whereas it was about 85% after 13 days in the absence of water. Suitable zeolites disclosed in Garwood are ZSM-5, ZSM-11, ZSM-35, ZSM-38 and include highly siliceous aluminosilicates where the silica/alumina ratio may range up to about 350 or more. U.S. Pat. No. 4,254,295 to Tabak discloses the oligomerization of olefins ranging up to about $C_{12}$ in which the oligomerization reaction is carried out in the liquid phase over ZSM-12 at a temperature of about 80°–400° F.

In addition to the use of zeolites such as described in the above-mentioned patents, silicalite is also useful in oligomerization reactions as disclosed in U.S. Pat. No. 4,414,423 to Miller, as well as in the aforementioned Miller U.S. Pat. No. 4,417,088. The Miller '423 patent discloses a two-step oligomerization process involving the sequential use of two intermediate pore size molecular sieves in which gaseous olefins are first converted to liquid olefins which are further oligomerized to higher molecular weight products.

Finally, U.S. Pat. No. 4,451,685 to Nevitt discloses the conversion of $C_2$–$C_3$ olefin feedstock to a gasoline blending stock over a crystalline borosilicate molecular sieve catalyst.

The octane number of the olefinic gasoline blending stock obtained by the above-cited processes is not sufficient and therefore requires addition of lead-free gasoline additives such as methyl tert-butyl ether and/or tert-amyl methyl ether. Thus, there is a need in the art for a process for the production of gasoline having an improved octane number which would require a lesser amount of anti-knock additive or even no anti-knock additive at all.

An object of the invention is to provide a process for the production of gasoline having an improved octane number from a feedstock containing substantially no isoolefins.

Still another object is to provide a process for producing gasoline which requires a lesser amount of anti-knock additive or even no anti-knock additive at all.

In accordance with the present invention, there is provided a new and improved multi-step olefin oligomerization process for the production of gasoline of high octane number. In carrying out the invention, a $C_2$–$C_6$ olefin containing feedstock which contains substantially no isoolefins is supplied to a first reaction zone. Within the first reaction zone the feedstock is contacted with an intermediate pore size siliceous crystalline molecular sieve catalyst under temperature and pressure conditions to effect oligomerization of the olefins in the feedstock. The oligomerization reaction produces a product having higher molecular weight hydrocarbons in the gasoline range and which contains isoalkenes. The oligomerized production from the first reaction zone is applied to a second reaction zone containing an acid cation exchange catalyst. Methanol is also supplied to the second reaction zone. The second reaction zone is operated at temperature and pressure conditions to effect etherification of isoalkenes to produce an etherified product effluent containing methyl ethers of hydrocarbons. The etherified product is then treated to recover a gasoline product of enhanced octane number. It is preferred that the $C_2$–$C_6$ olefin content of the feedstock be at least 25%, and more preferably, that the feedstock be composed predominantly of a mixture of olefins and paraffins in the $C_2$–$C_6$ range containing substantially no isoolefins.

In a preferred embodiment of the invention, water is co-fed to the first reaction zone along with the olefin containing feedstock. In a further aspect of the invention, water is separated from the oligomerized product effluent from the first reaction zone prior to supplying the oligomerized product to the etherification reaction zone.

In yet another aspect of the invention, the product effluent from the etherification reaction zone is extracted with water to remove methanol in a water-methanol mixture. The methanol thus recovered can be separated from the water and passed directly to the etherification zone as a make-up stream, or the methanol may be retained in admixture with the water and passed to the oligomerization reaction zone.

The gasoline produced according to the process of the invention has an unexpectedly improved octane number.

The present invention advantageously produces gasoline which has a highly improved octane number over that of gasoline produced by oligomerization processes over intermediate pore size siliceous crystalline molecular sieve catalysts as described previously. Under preferred conditions, the process of the invention has even yielded gasoline which has an octane number at least as good as that of gasoline obtained by standard oligomerization processes over phosphoric acid-containing catalysts. This is all the more unexpected in that etherification of this latter gasoline does not improve its octane number.

As will be shown hereinafter, the advantages of the process of the invention result from the combination of steps as described.

The feedstocks employed in the present invention contain one or more olefins having from 2–6 carbon atoms and contains substantially no isoolefins. While as described below, the olefinic feedstock normally may be composed of a mixture of iso- and normal-olefins and alkanes, the present invention can be carried out employing a feedstock which contains only a single olefin within the $C_2$–$C_6$ range.

Especially desirable feedstocks for use in the present invention are those having a substantial, and preferably, predominant (more than 50 wt. %), $C_4$ hydrocarbon fraction containing a mixture of butanes and butenes and containing substantially no isobutene. The butene content is preferably higher than the butane content. An especially preferred feedstock for use in the invention is the residual product recovered from an MTBE production unit in which isobutylene is reacted with methanol to produce methyl tert-butyl ether. The residual product remaining after the recovery of methyl tert-butyl ether will, aside from the utilization of isobutylene, not be substantially modified relative to the feedstock of the MTBE unit and will have an n-butene concentration greater than the iso-butene content. The residual is particularly suitable for the production of a gasoline range product of enhanced octane number in accordance with the present invention.

A preferred feed used for the process of the invention can be characterized as a mixture of butanes and butenes, comprising:

isobutane from 0 to about 40 wt. %;
n-butane from about 5 to about 30 wt. %;
1-butene from about 10 to about 30 wt. %;
2-butenes from about 15 to about 35 wt. %;
isobutene from 0 to about 5 wt. %;
and no more than 10%, and preferably, no more than 5% of lighter and/or heavier hydrocarbons.

The composition of the feedstock will vary according to its origin. Typical feeds are isobutene-free $C_4$ feeds from MTBE production units as described above $C_4$ cuts from catalytic cracking plants, or $C_4$ cuts from steam cracking units (after removal of butadiene) are increasingly used for the production of MTBE by the reaction of isobutene with methanol, whereby residual products are obtained comprised mostly of a mixture of butanes and n-butenes in roughly equal weight amounts. Such mixtures are preferred feeds for the process of the invention. As noted above, these preferred feeds are substantially free of isobutene by virtue of the reaction of isobutene with methanol to produce methyl tertiary butylether. As a practical matter, the isobutene content of such mixtures will be no more than 5 wt. % and usually the isobutene will be present in even lower concentrations of about 2 wt. % or less.

The oligomerization reaction is carried out on an intermediate pore size siliceous crystalline molecular sieve as known in the art.

These materials have the ability of sorting molecules based on the size and/or on the shape of the molecules. Intermediate pore size siliceous crystalline molecular sieves have the unique characteristics of being able to differentiate between large molecules and molecules containing quaternary carbons on the one hand, and smaller molecules on the other. By intermediate pore size, as used herein, is meant an effective pore aperature in the range of about 0.5 to 0.65 nm (nanometer) when the molecular sieve is in the H-form. The preferred effective pore size range is from about 0.53 to 0.62 nm. For a further description of siliceous crystalline molecular sieve catalysts of intermediate pore size and which may be used in carrying out the invention, reference is made to the aforementioned U.S. Pat. No. 4,417,088 to Miller, the entire disclosure of which is incorporated herein by reference.

The preferred catalysts for use in the oligomerization reaction are silica polymorphs and more specifically, highly siliceous crystalline molecular sieves of the silicalite type. Where silicalite type catalysts are employed, it is preferred to use a halogen stabilized silicalite. Such halogen stabilized silicalites are prepared by, prior to the use of the catalyst in the oligomerization reaction, stabilizing silicalite with a chlorine, bromine or fluorine containing stabilizing agent. Such halogen stabilized catalysts of the silicalite type are disclosed in U.S. patent application Ser. No. 008,878, entitled "HALOGEN STABILIZED CATALYSTS OF THE SILICALITE TYPE", filed by the present applicants on even date herewith. For a further description of halogen stabilized silicalite catalysts and their preparation, the entire disclosure of said U.S. patent application Ser. No. 008,878 is incorporated herein by reference.

The oligomerization step may also be carried out over zeolites, as described in the prior art; zeolites having a low Al:Si ratio being preferred. However, the gasoline recovered at the end of the process of the invention has less octane number enhancement when zeolites are used in the oligomerization step.

Water may be added in the oligomerization step because it usually improves the stability of the catalyst used. Also, the octane number of the gasoline obtained by the process of the invention is usually improved by the use of water in the oligomerization step.

The oligomerization reaction is carried out under well known oligomerization conditions. Typically, the pressure may be from atmospheric to about 60 bars (6 MPa), preferably from 3 to 20 bars (0.3 to 2 MPa), and most preferably, of about 15 bars (1.5 MPa). Higher pressures tend to give higher gasoline yields, while lower pressures tend to improve the octane number of the gasoline. Applicants have determined that the highest pressures, up to 60 bars (6 MPa), should only be used if the catalyst is stabilized halogenated silicalite. Another consideration is that the magnitude of pressure used in the oligomerization step, from an economical point of view, preferably, would be equal to that of the pressure used in the etherification step.

The temperature in the oligomerization step is typically from 200° C. to 500° C., but preferably from 250° C. to 450° C. and most preferably, of about 350° C. if silicalite (whether stabilized or not) is used, and preferably, from about 200° C. to 350° C., and most preferably, of about 280° C. if zeolite is used.

The liquid hourly space velocity of the feed (LHSV) is typically from 2 to 20 hr.$^{-1}$, but the LHSV may be as high as 50 hr.$^{-1}$.

When water is used in the oligomerization step, it is usually added in a molar water:feed ratio of 0.5 to 1.5, preferably of 0.5 to 1.0 and most preferably, of about 0.7. However, the advantages resulting from the addition of water must be balanced with economic considerations of handling large amounts of water, and the lowest possible amount of water consistent with the desired results is therefore preferred.

The oligomerization step of the present invention is more efficient with small crystallite sieve particles than with larger crystalline particles. Preferably, the molecular sieve crystals or crystallites are less than about 10 micrometers. Methods for making molecular sieve crystals in different physical size ranges are known to the art.

The molecular sieve crystallites can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones, as well as during the oligomerization. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins, reducing to a large degree the benefits of the invention.

If water was used in the oligomerization step, it must be removed from the effluent in the next step. Removal of the water is best achieved by first decanting the water, then drying the hydrocarbon mixture. No hydrocarbon separation is normally allowed to take place during this step. Nevertheless, if such is desired, normally gaseous hydrocarbons may be totally or partially separated from normally liquid hydrocarbons and removed from the effluent, for example, to recover isobutene which may, e.g., be transformed into polyisobutene. The octane number of the gasoline obtained by the process of the invention is, however, not as good as if such separation has been carried out. Normally gaseous hydrocarbons, as used herein, are all hydrocarbons up to $C_4$, which are gaseous at room temperature under atmospheric pressure.

Methanol is then added to the hydrocarbon mixture in essentially an equimolar amount, relative to the isoolefins contained in the hydrocarbon mixture. Examples of this are a molar ratio of methanol to isoolefins of 0.9:1-1:0.9, preferably 0.95:1-1:0.95, particularly preferably, about 1:1. For a given feed and given oligomerization conditions, the amount of isoolefins in the effluent may be estimated experimentally from an analytical determination of $C_4$ to $C_7$ isoolefins in the mixture.

The etherification step is carried out in a known manner on an acid cation exchange material, for example, on a styrene/divinylbenzene copolymer containing sulphonic acid groups, in a solid or suspended layer at a temperature of 30° C. to 120° C., preferably, 40° C. to 90° C., and under a pressure of 1 to 50 bars, preferably, 3 to 20 bars, and most preferably, of about 15 bars with a liquid hourly space velocity (LHSV) of 0.05 to 10 liters of total feed materials per liter of cation exchange material per hour, and preferably, an LHSV of about 1 hr.$^{-1}$. At high values of LHSV, the etherification yield tends to worsen, while significant amounts of dimethyl ether are produced at low values of LHSV. In this reaction, the pressures and temperatures mentioned are so adjusted relative to one another that the etherification reaction proceeds in liquid phase. Other catalysts may, of course, also be used in carrying out the invention. For example, the etherification catalysts disclosed in the aforementioned U.S. Pat. Nos. 4,503,263 and 4,503,265 may also be employed as catalysts in the etherification reaction. After passing through the etherification stage, the residual methanol is separated from the etherified product. As described below, the methanol is extracted by adding water to the effluent from the etherification step. The methanol may either be recovered by distillation of the methanol-water mixture and/or recycled by introducing the mixture instead of or in addition to the water of the oligomerization step. The methanol-free effluent is fed into a distillation column where the gasoline is separated from the remaining $C_3$ and $C_4$ hydrocarbons. This column has, for example, 30 to 80, and preferably, 40 to 70 plates. It can be designed as a bubble cap column or as a sieve tray column or any other distillation column with trays or packing materials which provide sufficient separating performance. This distillation column is operated under a pressure of 1 to 10 bars, preferably, 3 to 7 bars, and more preferably, 4 to 6 bars.

The gasoline thus recovered has an improved octane number.

A preferred form of plant operation according to the process of the invention will now be described, by way of example only, with reference to the accompanying FIGURE which is a flow diagram of an installation for carrying out the process of the invention.

Referring to the FIGURE, a $C_2$-$C_6$ olefin feedstock and water are supplied through lines 1 and 2, respectively, to the oligomerization reactor 3. This reactor can be, for example, a fixed-bed reactor or a tube reactor, and it can be used upflow or downflow, but preferably, upflow, as shown. The output from reactor 3 is fed through line 4 into a decanter free water knockout 5, where most of the condensed water is recovered via line 6, and then through line 7 to a drying unit 8.

The dried hydrocarbon mixture coming through line 9 is then mixed with methanol supplied via line 10 and introduced into the etherification reactor 11. This reactor can be, for example, a fixed-bed reactor or a tube reactor, and it can be used upflow or downflow, but preferably, upflow as shown.

The etherified product from reactor 11 is supplied through line 12 where it is mixed with water from line 16 and introduced into a decanter 17. The hydrocarbon mixture is fed through line 18 into a distillation column 20. Gasoline is recovered as bottom product of the distillation column through line 14, while the top product recovered through line 15 consists essentially of a mixture of $C_3$ and $C_4$ hydrocarbons.

In the decanter 17, the water extracts the methanol, and the water-methanol mixture is fed through pipe 19 and mixed with fresh water supplied via line 21 before being recycled into the oligomerization reactor 3.

The invention will now be described by way of the following examples which are intended to be illustrative and are not intended to limit the scope of the present invention.

EXAMPLE 1

Silicalite was loaded in a reactor and heated at 500° C. during 3 hours under a nitrogen flow at a gaseous hourly space velocity (GHSV) of 500 hr.$^{-1}$. The temperature was then lowered to 280° C. while maintaining the nitrogen flow saturated with $CCl_4$ for a period of 4 hours to produce stabilized halogenated silicalite.

A hydrocarbon feed, mixed with water in a molar ratio water:feed of 7:10, was passed over stabilized halogenated silicalite at a temperature of 380° C., under a pressure of 15 bars (1.5 MPa) and at an LHSV of 30 hr.$^{-1}$.

The composition of the hydrocarbon feed was as follows:

|  | (weight %) |
| --- | --- |
| propane | 1.71 |
| propylene | 0.09 |
| isobutane | 27.87 |
| n-butane | 12.16 |
| butenes | 58.09 |
| higher hydrocarbons | 0.08 |

After decantation of the water and drying, the resulting hydrocarbon mixture was then mixed with methanol in a weight ratio methanol:hydrocarbon mixture of 3:10, then passed into the etherification reactor containing as catalyst a Duolite ES-276 resin (Duolite is a trademark of Diamond Shamrock Corporation), ES-276 resin is a strongly acidic total sulfonated porous styrene-divinylbenzene copolymer beads with a total exchange capacity of 1.8 mol. $H^+$ per liter at a temperature of 80° C., under a pressure of 15 bars (1.5 MPa) and at LHSV 1 hr.$^{-1}$.

The etherified effluent was then distilled to yield as bottom product a gasoline having the following characteristics:

TABLE I

| Ethers in Gasoline | |
| --- | --- |
| MTBE | 16.7 wt. % |
| TAME (t-amyl methyl ether) | 19.7 wt. % |
| methyl tert-hexyl ether | 6.0 wt. % |
| methyl tert-heptyl ether | 3.1 wt. % |
| Octane Number | |
| RON (Research octane number) | 97.2 |
| MON (Motor octane number) | 82.9 |
| Density (gms/cc) | 0.745 |

Comparative Example 1

The procedure of Example 1 was repeated up to the decantation of the water and drying after the oligomerization step. The gasoline recovered was stored at atmospheric pressure until its testing.

The gasoline had the following characteristics:

TABLE II

| Octane Numbers: | RON | 89.0 |
| --- | --- | --- |
|  | MON | 78.2 |
| Density |  | 0.710 |

Comparative Example 2

The same feed as in Example 1 was submitted to polymerization over phosphoric acid-containing catalyst. The RON of the gasoline obtained was of 96.5.

This gasoline was then submitted to an etherification under the conditions described in Example 1. After etherification, the RON was of 96.0.

This comparative example shows that etherification of gasoline obtained by classical procedures does not improve its octane number.

EXAMPLE 2

Stabilized halogenated silicalite was prepared as described in Example 1.

The same feed as in Example 1, mixed with water in a molar ratio water/feed of 0.72, was passed over stabilized halogenated silicalite at a temperature of 341° C. under a pressure of 14.9 bars (1.49 MPa) and at LHSV 30.7 hr.$^{-1}$.

The water removal and etherification procedures described in Example 1 were carried out and the gasoline recovered had the following characteristics:

TABLE III

| Ethers in Gasoline | |
| --- | --- |
| MTBE | 9.5 wt. % |
| TAME | 4.9 wt. % |
| heavier ethers | 11.0 wt. % |
| Octane Numbers | |
| RON | 98.0 |
| MON | 82.7 |

Comparative Example 3

The procedure of Example 2 was repeated up to the decantation of the water and drying after the oligomerization step. The gasoline recovered was stored at atmospheric pressure until its testing, which indicated octane numbers of RON=93.4 and MON=80.0.

EXAMPLE 3

Silicalite was loaded into a reactor and heated at 500° C. during 3 hours under a nitrogen flow with a GHSV of 500 hr.$^{-1}$. The temperature was then lowered to 285° C. while maintaining the nitrogen flow saturated with CCl$_4$ for a period of 110 minutes to produce stabilized halogenated silicalite.

A hydrocarbon feed, mixed with water in a molar ratio water:feed of 7:10, was passed over the stabilized halogenated silicalite at a temperature of 320° C. under a pressure of 15 bars (1.5 MPa) and at LHSV 30.

The composition of the hydrocarbon feed was as follows:

|  | (weight %) |
| --- | --- |
| propane | 0.77 |
| propylene | 0.17 |
| isobutane | 40.03 |
| n-butane | 11.77 |
| butenes | 46.98 |
| higher hydrocarbons | 0.28 |

After decantation of the water, drying, and separation of the normally gaseous hydrocarbons, the resulting hydrocarbon mixture was mixed with methanol in a weight ratio methanol:hydrocarbon mixture of 1:10, then passed over an Amberlyst 15 resin (strongly acidic sulfonated porous styrene-divinylbenzene copolymer beads) at a temperature of 75° C., under a pressure of 15 bars (1.1 MPa) and at LHSV 1 hr.$^{-1}$. (Amberlyst is a trademark of Rohm & Haas).

The etherified effluent was distilled, yielding as bottom product a gasoline having the following characteristics:

TABLE IV

| Ethers in Gasoline | |
| --- | --- |
| MTBE | 0.4 wt. % |
| TAME | 4.9 wt. % |
| C$_7$ and higher ethers | 11.0 wt. % |
| Octane Numbers | |
| RON | 95.8 |
| MON | 81.5 |

EXAMPLE 4

A hydrocarbon feed, mixed with water in a molar ratio water:feed of 1:1, was passed over silicalite at a temperature of 310° C., under a pressure of 2 bars (0.2 MPa) and at LHSV 40 hr.$^{-1}$.

The composition of the hydrocarbon feed was as follows:

|  | (weight %) |
| --- | --- |
| C$_3$ hydrocarbons | 0.9 |
| isobutane | 32.5 |
| n-butane | 11.8 |
| n-butenes | 53.8 |
| isobutene | 1.0 |

After decantation of the water and drying, the resulting hydrocarbon mixture was mixed with method in a weight ratio methanol:hydrocarbon mixture of 15:100, then passed in the etherification reactor containing Amberlyst 15 (as described in Example 3) at a temperature of 75° C., under a pressure of 15 bars (1.5 MPa) at LHSV 1.

The etherified effluent has been distilled, giving an bottom product a gasoline having the following characteristics:

TABLE V

| Ethers in Gasoline | |
| --- | --- |
| MTBE | 14.4 wt. % |
| TAME | 4.4 wt. % |
| higher ethers | 6.5 wt. % |
| Octane Numbers | |
| RON | 97.0 |
| MON | 82.3 |

EXAMPLE 5

Propylene and steam in a molar ratio water/feed of 0.72 were mixed together and passed over silicalite at 309° C., under a pressure of 0.8 bar, and with a weight hourly space velocity (WHSV) of 97.2 hr.$^{-1}$.

After decantation of water and drying, the resulting hydrocarbon mixture was mixed with methanol in a weight ratio methanol:hydrocarbon mixture of 3:10, and then passed to the etherification reactor as described in Example 1.

The etherified effluent was distilled, yielding as bottom product a gasoline having a research octane number of 96.8.

EXAMPLES 6A, B and C

The process of the invention was carried out using C$_5$ and C$_6$ feeds as shown below in Table VI. The oligomerization step was performed over unmodified silicalite at the conditions disclosed in Table VI. The etherification step was carried out as described in Example 1. After distillation of the etherified effluent, the research octane number of the gasoline was determined.

TABLE VI

| Example | A | B | C |
| --- | --- | --- | --- |
| Feed | 1-pentene | 1-pentene | 1-hexene |
| wt. % | 94.9 | 94.9 | 97.1 |
| balance | other pentenes | other pentenes | other hexenes |
| Silicalite Oligomerization | | | |
| pressure | atmospheric | atmospheric | atmospheric |
| temperature | 310° C. | 350° C. | 350° C. |
| LHSV | 20 h$^{-1}$ | 20 h$^{-1}$ | 20 h$^{-1}$ |
| H$_2$O/feed ratio | 0.9 mol/mol | 0.9 mol/mol | 0.85 mol/mol |
| 1-alkene conversion | 96.8 wt. % | 97.3 wt. % | N.D. |
| After Etherification | | | |
| RON | 97.0 | 97.4 | 97.7 |

Having described specific embodiments of the present invention, it will be understood that modification thereof may be suggested to those skilled in the art, and it is intended to cover all much modifications as fall within the scope of the appended claims.

We claim:

1. In a process for the production of gasoline involving the oligomerization of olefins to higher molecular weight hydrocarbons, the steps comprising:
   a) passing a $C_2-C_6$ olefin containing feedstock into a reaction zone and into contact with an intermediate pore size siliceous crystalline molecular sieve catalyst;
   b) operating said reaction zone at a temperature and pressure conditions to effect oligomerization of olefins in said feedstock containing substantially no isoolefins to produce a product having higher molecular weight hydrocarbons in the gasoline range and an increased content of isoalkenes;
   c) supplying methanol and the oligomerized product effluent from the first reaction zone containing isoalkenes to a second reaction zone containing an acid cation exchange catalyst;
   d) operating said second reaction zone at temperature and pressure conditions to effect etherification of said isoalkenes in said oligomerized product to produce an etherified product effluent from said second reaction zone containing methyl ethers of hydrocarbons in said mixture; and
   e) recovering a gasoline product of improved octane number from said etherified product.

2. The method of claim 1 further comprising the step of co-feeding water to said first reaction zone along with said olefin containing feedstock.

3. The method of claim 2 wherein the water co-feed is supplied in an amount to provide a molar ratio of water to hydrocarbons in said feedstock within the range of 0.5–1.5.

4. The method of claim 3 wherein said molar ratio of water to hydrocarbons is within the range of 0.5–1.0.

5. The method of claim 3 wherein said molar ratio of water to hydrocarbons is about 0.7.

6. The method of claim 2 further comprising the step of separating water from the oligomerized product from said first reaction zone prior to supplying said oligomerized product to said etherification reaction zone.

7. The method of claim 1 further comprising the step of treating the oligomerized product from said first reaction zone to separate at least a portion of the normally gaseous hydrocarbons therein from said oligomerized product prior to passing said oligomerized product to the etherification zone.

8. The process of claim 1 wherein the $C_2-C_6$ olefin content of the olefinic feedstock is at least 25%.

9. The process of claim 8 wherein said olefin feedstock is composed predominantly of a mixture of olefins and paraffins in the $C_2-C_6$ range.

10. The method of claim 1 further comprising the step of separating methanol from the etherified product of (d) by extraction with water to produce a water-methanol mixture and recycling methanol thus recovered to the etherification zone.

11. The process of claim 1 wherein said olefin containing feedstock contains a substantial amount of a butene fraction.

12. The process of claim 11 wherein said olefin containing feedstock is predominantly a butene fraction.

13. The method of claim 1 wherein said feedstock is composed predominantly of $C_4$ hydrocarbons comprising a mixture of butane and butene fractions.

14. The method of claim 13 wherein said mixture of butane and butene fractions comprises at least 90% of said feedstock.

15. The method of claim 14 wherein said mixture of butane and butene fractions comprises at least 95% of said feedstock.

16. The method of claim 13 wherein said feedstock contains more butenes than butanes.

17. The method of claim 1 wherein the gasoline product of step (e) is recovered from said etherified product by a fractional distillation procedure in which a low boiling fraction is removed from said etherified product to produce said gasoline product.

18. The method of claim 17 further comprising the step, prior to said distillation procedure, of separating methanol from said etherified product.

19. The process of claim 18 wherein the methanol separation step is carried out by the extraction of said etherified product with water to produce a water-methanol mixture and recycling said water-methanol mixture to the first reaction zone.

20. The process of claim 18 wherein low boiling fraction removed in said distillation procedure is composed predominantly of $C_3-C_4$ hydrocarbons.

21. The method of claim 1 wherein said olefin containing feedstock contains a butene-butane mixture.

22. The method of claim 21 wherein the butene concentration of said feedstock is higher than the butane concentration of said feedstock.

23. The method of claim 21 wherein the oligomerization step in the first reaction zone is carried out at a temperature within the range of 200°–500° C., a pressure within the range of 1–60 bars, and a space velocity (LHSV) within the range of 2–50 hour.$^{-1}$.

24. The method of claim 23 wherein said oligomerization step is carried out at a pressure within the range of 3–20 bars.

25. The method of claim 23 wherein said molecular sieve catalyst is silicalite.

26. The method of claim 25 wherein said oligomerization step is carried out at a temperature within the range of 250°–450° C.

27. The process of claim 23 wherein said molecular sieve catalyst is halogen stabilized silicalite.

28. The process of claim 23 wherein said molecular sieve catalyst is an aluminosilicate zeolite.

29. The method of claim 28 wherein said oligomerization step in said first reaction zone is carried out at a temperature within the range of 200°–350° C.

30. The process of claim 21 wherein said methanol is supplied to said second reaction zone in substantially an equal molar amount relative to the isoalkenes in said oligomerized product.

31. The method of claim 21 wherein the etherification step in said second reaction zone is carried out at a temperature within the range of 30°–120° C., a pressure within the range of 1–50 bars, and a space velocity (LHSV) within the range of 0.5–10 hr.$^{-1}$.

32. The method of claim 31 wherein said etherification step is carried out at a temperature within the range of 40°–90° C., a pressure within the range of 3–20 bars, and a space velocity (LHSV) of about 1 hr.$^{-1}$.

33. In a process for the production of gasoline involving the oligomerization of olefins to higher molecular weight hydrocarbons, the steps comprising:
   (a) passing a $C_2-C_6$ olefin containing feedstock having a normal olefin content and an isobutene content into a first reaction zone for reaction of isobutene with methanol to produce methyl tert-butyl ether;

(b) withdrawing a product stream from said first reaction zone and recovering methyl tert-butyl ether therefrom to produce a residual olefin containing product stream;

(c) passing said residual olefin containing product stream into a second reaction zone and into contact with an intermediate pore size siliceous crystalline molecular sieve catalyst;

(d) operating said second reaction zone at temperature and pressure conditions to effect oligomerization of olefins in said residual stream to produce a product having higher molecular weight hydrocarbons in the gasoline range and an increased content of isoalkenes;

(e) supplying methanol and the oligomerized product effluent from the second reaction zone containing isoalkenes to a third reaction zone containing an acid cation exchange catalyst;

(f) operating said third reaction zone at temperature and pressure conditions to effect etherification of said isoalkenes in said oligomerized product to produce an etherified product effluent from said third reaction zone containing methyl ethers of hydrocarbons in said mixture; and (g) recovering a gasoline product of improved octane number from said etherified product.

34. The method of claim 33 wherein the residual olefin containing product stream passed to said second reaction zone contains no more than 2 wt. % isobutene.

35. The method of claim 33 further comprising the step of co-feeding water to said second reaction zone, along with said residual product stream.

* * * * *